US006994680B1

(12) United States Patent
Aponte

(10) Patent No.: US 6,994,680 B1
(45) Date of Patent: Feb. 7, 2006

(54) AUTOMATED BACK AND BELLY SCRATCHER

(76) Inventor: Gina Aponte, 3511 Henrietta Ave., LaCrescenta, CA (US) 91214

( * ) Notice: Subject to any disclaimer, the term of this patent is extended or adjusted under 35 U.S.C. 154(b) by 0 days.

(21) Appl. No.: 11/178,953

(22) Filed: Jul. 11, 2005

Related U.S. Application Data

(60) Provisional application No. 60/587,686, filed on Jul. 14, 2004.

(51) Int. Cl.
*A61F 7/00* (2006.01)

(52) U.S. Cl. ........................................ 601/137; 601/136

(58) Field of Classification Search .................. 601/93, 601/95, 97, 101, 103, 136, 137–138, 143–147
See application file for complete search history.

(56) References Cited

U.S. PATENT DOCUMENTS 4,091,805 A * 5/1978 Clark .......................... 601/80
4,574,788 A 3/1986 Jordan ......................... 128/67
5,445,596 A * 8/1995 Grace .......................... 601/154
5,904,661 A * 5/1999 Bonz et al. ................. 601/137
D443,114 S 5/2001 Burrell et al. ............ D28/91.2
6,656,139 B2 * 12/2003 Zwezdaryk .................. 601/46
6,830,552 B1 * 12/2004 Gonzalez .................... 601/137

* cited by examiner

*Primary Examiner*—Michael A. Brown
(74) *Attorney, Agent, or Firm*—Goldstein Law Offices, P.C.

(57) ABSTRACT

An automated back and belly scratcher having a telescopically adjustable shaft and having a hand-shaped portion attached at one end of the shaft. The hand-shaped portion has fingers that may be used for scratching or massaging the back or belly of a user or of a pet such as a dog or a cat. The shaft has a plurality of segments which may be telescopically positioned within one another, in order to maximally extend the shaft, or alternately, to retract the shaft into a storage position. The back and belly scratcher is provided with a motor in mechanical contact with the fingers of the hand-shaped portion, thereby enabling a user to selectively move the fingers by activating the motor. The motor has two modes of operation, one that produces a repetitive finger motion comprising successively and sequentially tapping each of the different fingers, in turn, and one that comprises simultaneous in-and-out finger motion of all of the fingers.

8 Claims, 1 Drawing Sheet

AUTOMATED BACK AND BELLY SCRATCHER

CROSS REFERENCES AND RELATED SUBJECT MATTER

This application is a continuation of provisional patent application Ser. No. 60/587,686 filed in the United States Patent Office on Jul. 14, 2004.

BACKGROUND OF THE INVENTION

1. Field of the Invention

The invention generally relates to a back scratcher, and in particular relates to an automated back and belly scratcher having a telescopically adjustable shaft and having a hand-shaped portion for scratching the back and belly of a user or of a pet.

2. Description of the Related Art

A variety of backscratchers are available for moving a contact surface against hard-to-reach areas upon a person's back. However, these back scratchers have a number of substantial limitations. In particular, most existing back scratchers are manually operated and have "scratching portions" which are rigid and incapable of motion. This may not present a serious problem if the scratcher is used only intermittently, or for a short period of time. However, manually scratching the back or belly of a user or of a pet such as a dog or a cat may become difficult and tiring after an extended period of time. Accordingly, there is a need for an automated back and belly scratcher having a hand-shaped portion having fingers, and having a motor contained within the hand-shaped portion for selectively moving the fingers, in order that the user can scratch the back or belly of the user or of a pet for an extended period of time without becoming tired.

A large variety of back scratchers have been devised. By way of example, U.S. Pat. No. 5,904,661 to Bonz appears to show a backscratcher comprised of a motor-driven telescoping arm having an end portion having fingers. Additionally, U.S. Pat. No. 4,574,788 to Jordan appears to show a back scratcher comprising a rigid elongated rod having a handle affixed thereunto, having a scratcher head having a plurality of tines, and having a base assembly for selectively mounting the back scratcher in an upright position while being stored. Moreover, United States Patent No. D443,114 to Burrell appears to show an ornamental design for a back scratcher device.

While these devices may be suitable for the particular purpose employed, or for general use, they would not be as suitable for the purposes of the present invention as disclosed hereafter.

SUMMARY OF THE INVENTION

It is an object of the invention to provide an automated back and belly scratcher that is well suited for scratching or massaging the back or belly of a user or of a pet such as a dog or a cat. Accordingly, the back and belly scratcher has a hand-shaped portion having elongated fingers that are well suited for scratching or massaging the back or belly of a user or of a pet.

It is another object of the invention to produce a back and belly scratcher having a hand-shaped portion having fingers which are capable of moving. Accordingly, the back and belly scratcher is provided with a motor in mechanical communication with the fingers of the hand-shaped portion, thereby enabling a user to selectively move the fingers of the hand by activating the motor.

It is yet another object of the invention to produce a back and belly scratcher that may be compactly stored when not being used. Accordingly, the back and belly scratcher has a telescopically adjustable shaft, thereby allowing the back and belly scratcher to be compactly stored when not being used.

Further objects of the invention will become apparent in the detailed description of the invention that follows.

The invention is an automated back and belly scratcher having a telescopically adjustable shaft and having a hand-shaped portion attached at one end of the shaft. The hand-shaped portion has fingers that may be used for scratching or massaging the back or belly of a user or of a pet such as a dog or a cat. The shaft has a plurality of segments which may be telescopically positioned within one another, in order to maximally extend the shaft, or alternately, to retract the shaft into a storage position. The back and belly scratcher is provided with a motor in mechanical contact with the fingers of the hand-shaped portion, thereby enabling a user to selectively move the fingers by activating the motor. The motor has two modes of operation, one that produces a repetitive finger motion comprising successively and sequentially tapping each of the different fingers, in turn, and one that comprises simultaneous in-and-out finger motion of all of the fingers.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
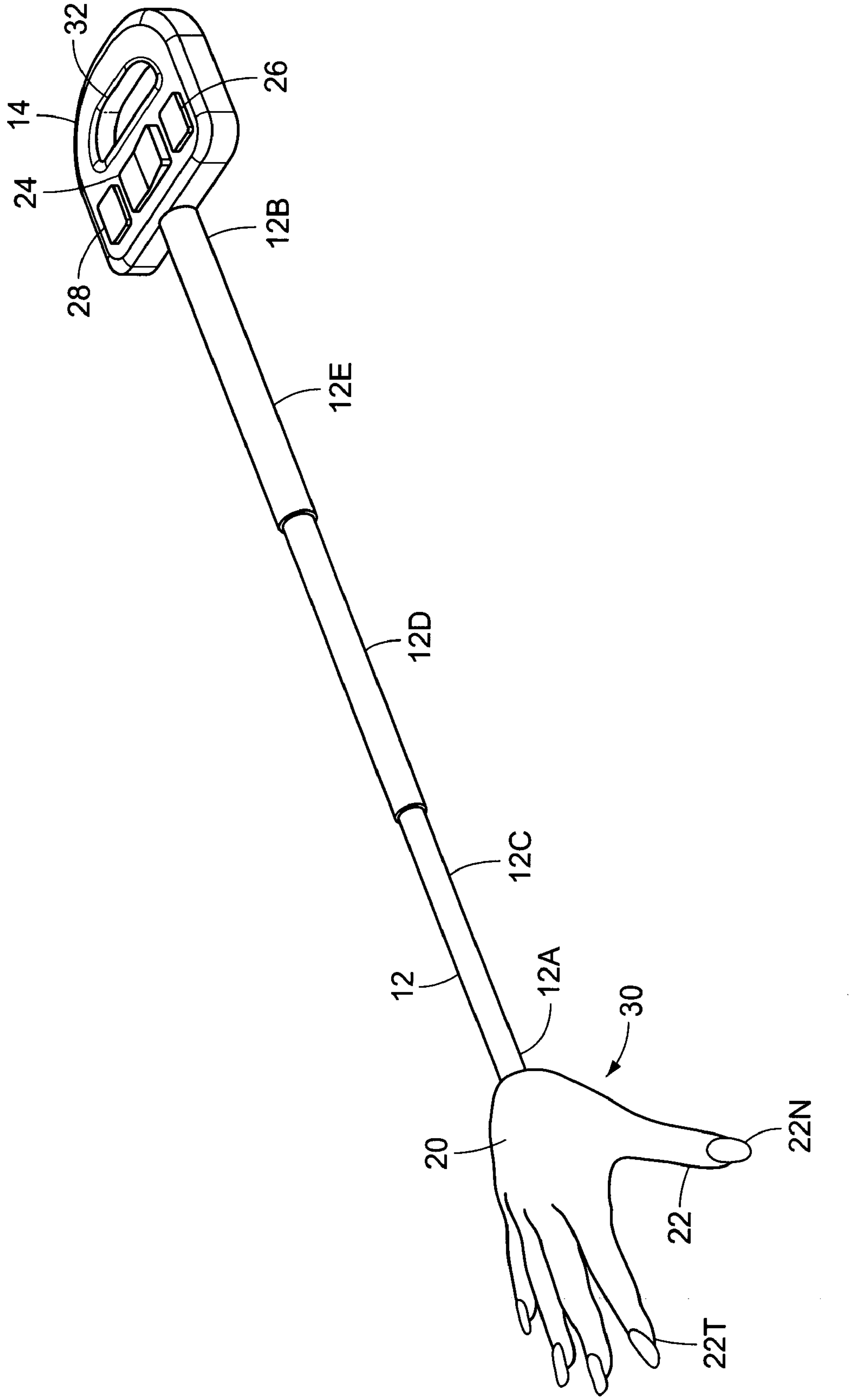
FIG. 1 is a perspective view of an automated back and belly scratcher wherein a shaft has been telescopically extended, wherein a motor has been activated, and wherein arrows indicate direction of motion of the fingers of a hand-shaped portion.

FIG. 1 illustrates an automated back and belly scratcher 10, having a shaft 12 having a first end 12A and a second end 12B, having a hand-shaped portion 20 affixed to the first end 12A, and having a handle 14 affixed to the second end 12B. The hand-shaped portion 20 has five fingers 22, each having a fingertip 22T having a fingernail 22N. The hand-shaped portion 20 contains a small motor 30 therein, for selectively moving the fingers 22, as will be described. The handle 14 is held within one of the hands of a user while using the hand-shaped portion 20 to scratch or massage the back or belly of a user or of a pet such as a dog or a cat.

The motor 30 of the back and belly scratcher 10 is in mechanical contact with the fingers 22 of the hand-shaped portion 20, thereby enabling the user to selectively move the fingers 22 by activating the motor 30. The motor 30 has two modes of operation. In particular, the motor 30 has a first mode of operation that produces a finger motion comprising successively and sequentially tapping each of the different fingers 22 of the hand-shaped portion 20, in turn, and has a second mode of operation that produces a finger motion comprising simultaneous in-and-out extension of all of the different fingers 22 of the hand-shaped portion 20. The means for producing said motions with a motor are well known to those of ordinary skill in the relevant art.

The handle 14 has an opening 32 extending fully therethrough, for enabling the user to firmly grasp the handle 14 while the scratcher 10 is being deployed. The handle 14 has an activation button 24 for selectively activating the scratcher 10. The handle 14 has a first finger motion button 28 for switching the motor 30 to the first mode of operation that produces a finger motion comprising successively and sequentially tapping each of the different fingers 22, in turn. The handle 14 also has a second finger motion button 26 for switching the motor 30 to the second mode of operation that produces a simultaneous in-and-out extension of all of the fingers 22 of the hand 20.

The shaft 12 is telescopically adjustable. In particular, the shaft 12 is comprised of several segments, 12C, 12D, and 12E, wherein segment 12D is capable of being selectively retracted within segment 12E, and wherein segment 12C is capable of being selectively retracted within segment 12D. This feature allows the user to adjust the overall length of the shaft 12, and also allows the user to store the scratcher 10 in a minimal storage volume.

The scratcher 10 is selectively powered by at least one battery, and the handle 14 contains a battery compartment for selective containment therein of said at least one battery.

The hand-shaped portion 20 of the scratcher 10 is provided in a variety of sizes. In particular, the hand-shaped portion 20 is provided in a version that is approximately four inches in size, and also a version that is approximately six inches in size. Each of the segments, 12C, 12D, and 12E, of the shaft 12 are approximately one foot in length. The shaft 12 is preferably constructed from a strong light metal, such as aluminum, but may be constructed from plastic. The hand-shaped portion 20 is preferably constructed from a soft material such as latex. The fingernails 22N are constructed from a hard acrylic, to facilitate scratching and massaging various body parts.

In use, a user adjusts the length of the shaft 12 by telescopically extending the segments, 12C, 12D, and 12E. The user activates the scratcher 10 by pressing the activation button 24. The user determines which of the various modes of operation of the motor 30 is to be used for scratching or massaging. In particular, the user produces a finger motion comprising successively and sequentially tapping each of the different fingers 22, in turn, by pressing the first finger motion button 26 of the handle 14 and thereby switching the motor 30 to the first mode of operation. The user produces a finger motion comprising simultaneous in-and-out extension of all of the fingers 22, by pressing the second finger motion button 26 of the handle 14 and thereby switching the motor 30 to the second mode of operation. The user holds the handle 14 within one of the hands of the user, and uses the hand-shaped portion 20 for scratching or massaging the back or belly of the user or of a pet. When finished using the scratcher 10, the user presses the activation button 24 in order to deactivate the scratcher 10. The user telescopically retracts the segments, 12C, 12D, and 12E, within one another, thereby allowing compact storage of the scratcher 10.

In conclusion, herein is presented an automated back and belly scratcher having a telescopically adjustable shaft and having a hand-shaped portion for scratching or massaging the back or belly of a user or of a pet. The invention is illustrated by example in the drawing figures, and throughout the written description. It should be understood that numerous variations are possible, while adhering to the inventive concept. Such variations are contemplated as being a part of the present invention.

What is claimed is:

1. An automated back and belly scratcher for scratching and massaging the back and belly of a user or of a pet, comprising:

a shaft having a first end and a second end;

a hand-shaped portion affixed to the first end of the shaft, having five fingers, each having a fingertip having a fingernail, said hand-shaped portion for scratching and massaging the back and belly of a user or of a pet;

a motor contained within the hand-shaped portion, and in mechanical contact with the fingers of the hand-shaped portion, for selectively moving the fingers, said motor having two modes of operation, namely:

a first mode of operation that produces a finger motion comprising successively and sequentially tapping each of the different fingers of the hand-shaped portion, in turn; and a second mode of operation that produces a finger motion comprising simultaneous in-and-out extension of all of the different fingers of the hand-shaped portion; and a handle affixed to the second end of the shaft, having an activation button for selectively activating the motor, a first finger motion button for switching the motor to the first mode of operation, and a second finger motion button for switching the motor to the second mode of operation.

2. The automated back and belly scratcher as recited in claim 1, wherein the shaft is telescopically adjustable, in order to allow the user to adjust the overall length of the shaft, and also to allow the user to store the scratcher in a minimal storage volume.

3. The automated back and belly scratcher as recited in claim 2, wherein the handle has an opening extending fully therethrough, for enabling the user to firmly grasp the handle while the scratcher is being deployed.

4. The automated back and belly scratcher as recited in claim 3, wherein the motor is selectively powered by at least one battery.

5. The automated back and belly scratcher as recited in claim 4, wherein the hand-shaped portion is constructed from a soft latex.

6. The automated back and belly scratcher as recited in claim 5, wherein the fingernails are constructed from a hard acrylic, to facilitate scratching and massaging various body parts.

7. The automated back and belly scratcher as recited in claim 6, wherein the shaft is constructed from a light metal.

8. The automated back and belly scratcher as recited in claim 6, wherein the shaft is constructed from plastic.

* * * * *